United States Patent

Ranieri et al.

[11] Patent Number: 5,252,728
[45] Date of Patent: Oct. 12, 1993

[54] PROCESS FOR OBTAINING POLYMERS WITH ANTIVIRAL ACTIVITY

[75] Inventors: Juan P. P. Ranieri; Antonio F. G. Gomez-Pamo; Luis C. Llamas, all of Madrid; Jesus A. Armendariz, Tres Cantos; Juan A. Leal Ojeda, Madrid; Carmen G. Benito, Segovia, all of Spain

[73] Assignee: Laboratorios Andromaco S.A., Madrid, Spain

[21] Appl. No.: 806,669

[22] Filed: Dec. 13, 1991

[30] Foreign Application Priority Data

Dec. 17, 1990 [ES] Spain .................. 9003222

[51] Int. Cl.$^5$ .................. A61K 31/715; C08B 37/00; C07H 1/00; C07H 3/00
[52] U.S. Cl. .................. 536/124; 536/18.5; 536/51; 536/53; 536/54; 536/55; 536/55.1; 536/126
[58] Field of Search .................. 536/124, 126, 18.5, 536/54, 55, 55.1, 51, 53

[56] References Cited

U.S. PATENT DOCUMENTS

| | | | |
|---|---|---|---|
| 3,856,775 | 12/1974 | Fukuoka et al. | 536/1.1 |
| 4,739,046 | 4/1988 | Di Luzio | 536/124 |
| 4,840,941 | 6/1989 | Ueno et al. | 514/54 |

FOREIGN PATENT DOCUMENTS 2627125 12/1976 Fed. Rep. of Germany .
1013902 12/1965 United Kingdom .

OTHER PUBLICATIONS

M. Baba et al., Antimic. Ag. Chemother. 32, 1742, 1988.
E. de Clercq, Trends in Pharmacol. Sci., 11, 198, 1990.
B. Alarcon et al., Antiviral Res., 4, 231, 1984.
M. E. Gonzalez et al., Antimic. Ag. Chemother., 31, 1388, 1987.
P. Ruperez et al., Trans. Br. Mycol. Soc., 80, 313, 1983.

Primary Examiner—Ronald W. Griffin
Attorney, Agent, or Firm—Ladas & Parry

[57] ABSTRACT

The present invention consists in a process for obtaining polymers with antiviral activity which is characterized in that beginning with oligo or polysaccharides with a specific structure, polymers with a specific number of carbonyl groups are obtained by oxidation; in that the carbonyl groups of the oxidized oligo/polysaccharides are made to react with amino groups of molecules carrying amino and sulfonated groups, such as aliphatic aminosulfonates, in water or in mixtures of water with water-miscible solvents, under specific temperature, time, and pH conditions, giving rise to polymers carrying sulfonated groups, which are purified by conventional processes; in that the sulfonated polymers thus obtained have antiviral activity and either lack or present very low toxicity and anticoagulant activity, and are thus suitable for the production of pharmaceutical preparations suitable for use in topical or systemic antiviral therapy in humans or in animals. It is applicable in the pharmaceutical industry.

15 Claims, No Drawings

PROCESS FOR OBTAINING POLYMERS WITH ANTIVIRAL ACTIVITY

The present invention concerns a process for obtaining polymers by controlled oxidation of polysaccharides and chemical reaction with molecules carrying amino and sulfonated groups, under specific temperature, pH, and time conditions, with the resultant polymers presenting antiviral activity, as a result of which they may be used in the galenic form appropriate to human or animal medicine.

The antiviral activity of sulfated polysaccharides, carrageenans, sulfated dextran, polysulfated pentosan, and fucoidin has been described in vitro and in vivo in experimental animals (M. Baba et al. Antimic. Ag. Chemother. 32, 1742, 1988). It has also been demonstrated that the distribution over a carbonated structure of groups sulfated with a specific spatial distribution produces compounds which present antiviral activity; however, to date, the activity of said compounds in vivo in dose and mode of application which can be used in humans has not been demonstrated (E. de Clercq, Trends in Pharmacol. Sci., 11, 198, 1990). The fundamental reasons for this lack of activity may be attributed to inadequate bioavailability and the appearance of undesirable side effects such as increased coagulation time and toxicity. This can be explained by the large molecular size of the specimens used, the anticoagulant properties of sulfated oligo/polysaccharides, and the presence of pyridine groups or quaternary amino derivatives as a consequence of the sulfating methods used.

Because of all this, various lines of investigation have been proposed aimed at finding sulfated oligosaccharides derived from sulfated oligo/polysaccharides which present antiviral activity without manifesting anticoagulant properties and whose bioavailability is better or can be improved based on recent new galenic techniques and at finding new sulfation techniques which do not involve the addition of molecules such as pyridine, which can affect the activity or the bioavailability or which increase the toxicity of the product.

The process according to the present invention describes the obtaining of polymers or oligomers with antiviral activity derived from oligo/polysaccharides and which present the advantages compared to others which are known for obtaining antiviral oligo/polymers, with the resulting active products also presenting very low or non-existent anticoagulant activity, presenting very low or non-existent toxicity, having no toxic contaminants or addition products, and being able to obtain oligomers of a molecular size sufficiently low to facilitate adequate bioavailability when they are applied in the appropriate galenic forms.

GENERAL DESCRIPTION OF THE PROCESS

The process according to the present invention consists in the oxidation of oligo/polysaccharides under controlled conditions to increase the number of carbonyl groups present and subsequent condensation of these with the amino groups of molecules carrying said groups as well as sulfonated groups, thus obtaining polymers which present sulfonic groups and have antiviral activity.

The starting material for performance of the process according to the invention can be any oligo/polysaccharide (hereinafter referred to as molecule 1). After molecule 1 is obtained (by extraction and purification of a natural source, by chemical synthesis, etc.), in a first step (preparation) one proceeds to suspend or dissolve it in a final quantity of 0.1 to 20 g L/1 in an appropriate solvent, for example, deionized water, 0.9%-solution of NaCl in deionized water, or dimethyl sulfoxide solution in deionized water at a concentration between 5 and 50%, and to wash it by ultrafiltration cycles through 500- to 5,000-dalton membranes and addition of solvent to the original volume. After washing, its suspension or solution is concentrated to 1:10 of the original volume and lyophilized.

In a second step (oxidation) one proceeds to suspend or dissolve molecule 1 in a solution of a soluble alkaline or alkaline-earth periodate with a concentration between 1 and 100 mM and pH between 7.0 and 9.0, such that the quantity of molecule 1 is between 0.1 and 10 g L/1. Said suspension or solution is incubated at a temperature between 14° and 35° C. under resting conditions or gentle agitation, and in darkness, for a period of 1 to 10 days. After said time, it is dialyzed between 12 and 48 hours against water at a temperature between 4° and 20° C. and lyophilized.

In a third step (condensation) the molecule 1 oxidized in step two is suspended or dissolved in an appropriate container provided with a cover in an appropriate solvent, for example, water, 0.9%-solution of sodium chloride in water, or dimethyl sulfoxide solution in water at a concentration between 5 and 20%, such that its quantity is between 0.1 and 10 g L/1. The molecule carrying the amino and sulfonated groups (hereinafter referred to as the molecule 2) suspended or dissolved in the appropriate solvent and with the pH of the solution adjusted between 1.5 and 8.5 is added to said suspension or solution under agitation, and in a sufficient quantity such that the ratio between the number of carbonyl groups of molecule 1 and the number of amino groups of molecule 2 is between 1:10 and 2:1. Said molecule 2 may be obtained from natural products, by synthesis, etc. Said reaction mixture is incubated under agitation at a temperature between 85° and 110° C. until the concentration of the molecule 2 becomes constant or zero.

In a fourth and final step (purification), the sulfonated polymer with groups present in the above reaction mixture is purified by conventional means such as gel filtration, ultrafiltration, dialysis, precipitation with solvents, etc.

EXAMPLE 1

Step 1: Dextran T-40 from Pharmacia Fine Chemicals, 1,6-α-glucan with an average molecular weight of 40 kd, is used as the starting material. 1 g of said product is dissolved in deionized water to a final concentration of from 1 to 10 g L/1 and ultrafiltered through a 1000-dalton membrane until the concentrate reaches a final volume of 1:5 to 1:20 of the original; water is added to restore the initial volume and ultrafiltration is repeated to the same level of concentration. This process is performed two more times. Upon conclusion, it is concentrated to a final volume of 1:5 to 1:20 of the original and lyophilized.

Step 2: The polysaccharide is dissolved in 10 to 50 mM $NaIO_4$ to a final concentration of 0.5 to 4 g L/1 and incubated at rest in darkness for 5 to 7 days at room temperature. Oxidation is monitored by the drop in absorption to 223 nm. The oxidized polysaccharide is dialyzed for 24 hours against running water to eliminate the excess periodate and lyophilized.

Step 3: The lyophilized product of the 2nd step is dissolved in an appropriate container provided with a lid in water to a final concentration of 0.5 to 4 g L/1 and the pH of the suspension is adjusted to 6.5 to 8.5; a solution of cysteic acid in water is added to a concentration of 5 to 10 g L/1 adjusted to pH 6.5 to 8.5, in a sufficient quantity that in the reaction mixture the cysteic acid is found in molar proportion between 0.5 and 2.0 with the number of aldehyde groups of the oxidized polysaccharide. This is incubated at 95° to 100° C. until the cysteic acid has been totally consumed or its concentration does not vary; the quantity of cysteic acid present is determined by means of an amino acid autoanalyzer.

Step 4: This is dialyzed against running water for 48 hours and lyophilized.

The product thus obtained is a brown, water-soluble powder, with a molecular weight between 8 and 60 Kd and the following elemental composition: $49\pm9\%$ O, $33\pm6\%$ C, $10\pm2\%$ S, $5\pm1\%$ H, and $4\pm1\%$ N, and it presents the following characteristics with regard to biological activity:

Said product is capable, under the conditions described below, of inhibiting the cytopathic effect of the Herpes Simplex 1 virus on He La cells "in vitro" at a concentration in the cellular culture between 10 and 150 µg mL/1. The conditions for the analysis of the antiviral effect, based on those described in B. Alarcón et al., Antiviral Res., 4, 231, 1984 and M. E. González et al., Antimic. Ag. Chemother., 31, 1388, 1987, are: -Cells and virus: The Herpes Simplex type 1 virus (KOS) was grown in Vero cells, in Dulbecco Modified Eagle Medium (DMEM) supplemented with 10% fetal calf serum (FCS) and containing 10,000 IU of penicillin and 50 mg of streptomycin per ml. The concentration of the virus was estimated by plaque test on Vero cells; plaque test: The cells were grown in a single layer until confluence in plaques P60 and were incubated serially with 0.5 ml of 1:10 dilutions of the virus in phosphate-buffered saline (PBS) supplemented with 0.5% FCS. After an absorption period of 1 hour at 37° C., the inoculum was removed and an overlay of 5 ml of DMEM with 0.6% agar and 2% FCS was added. The single layers were incubated at 37° C. in humidified air containing 6% $CO_2$ for several days until the appearance of cytopathic effects. After these appeared, the overlay was removed, the single layer of cells was precipitated with trichloroacetic acid (TCA) to 5% and the lysis plaques were counted; estimation of the cytopathic effect: Single layers of HeLa cells grown in DMEM with HSV1 were infected at a low rate of infection (0.0 to 0.4 plaque forming units (PFU)) in the presence of decreasing concentrations of product between 0 and 200 µg/ml. After 48 hours of incubation at 37° C., the cytopathic effects are studied in the cells, infected or not, by observation under a phase-contrast microscope.

Said product, injected intravenously in male SD rats at a dosage of 30 mg $kg^{-1}$ does not produce changes in coagulation time, conditions under which sodium heparinate totally prevents coagulation. Under said conditions, no external toxic manifestation is observed.

EXAMPLE 2

Step 1: The starting material is a 1,6-β-glucan polysaccharide obtained from *Penicillium erythromelis* as indicated in P. Rupérez et al., Trans. Br. Mycol. Soc., 80, 313, 1983, which is washed as indicated in step 1 of Example 1.

In steps 2, 3, and 4, one proceeds in the same manner as in Example 1.

The product thus obtained is a light brown, water-soluble powder capable of inhibiting "in vitro" the cytopathic effects of the viruses of encephalomyocarditis and vesicular stomatitis at concentrations in the culture medium between 10 and 150 and 20 and 200 µg mL/1 respectively. Said product does not present anticoagulant activity, tested under the conditions described for Example 1, nor under said conditions is there any external toxic manifestation.

We claim:

1. A process for obtaining polymers with antiviral activity, comprising the steps of:
    suspending or dissolving in a solvent an oligo/-polysaccharide, hereafter referred to as molecule (1), and cleansing the suspension or solution of any interfering substances by ultrafiltration;
    oxidizing the molecule (1) with an oxidizing agent to generate carbonyl groups and thereafter removing the oxidizing agent thereby providing an oxidized molecule (1);
    preparing a reaction mixture comprising the oxidized molecule (1) and a molecule carrying amino and sulfonated groups, hereafter referred to as molecule (2), and thereafter heating and incubating the reaction mixture to decrease the concentration of the molecule (2); and
    purifying the reaction mixture to provide a sulfonated polymer.

2. A process as claimed in claim 1 wherein the oligo/-polysaccharide is suspended in a solvent selected from the group consisting of deionized water, NaCl solution at 0.9% in deionized water, and dimethyl sulfoxide solution in deionized water at a concentration between 5 and 50%, the final quantity of oligo/polysaccharide in suspension being from 0.1-20 g $L^{-1}$.

3. A process as claimed in claim 1, wherein the ultrafiltration includes the use of membranes of 500 to 5000 dalton.

4. A process as claimed in claim 1 wherein oxidation of molecule (1) generates carbonyl atoms of between 20% and 90% of those that may be produced from vicinal diols existing in the molecule.

5. A process as claimed in claim 1 wherein the oxidizing agent is removed by dialysis.

6. A process as claimed in claim 1 wherein the reaction mixture is prepared in a container including a hermetic closure, molecule (2) is suspended in a solvent which is selected from the group consisting of water, sodium chloride solution at 0.9% in water, a solution of dimethyl sulfoxide in water at a concentration of between 5 and 20%, and the sulfonated polymer is purified by physicochemical processes selected from the group consisting of gel filtration, ultrafiltration and dialysis.

7. A process as claimed in claim 1 wherein molecule (1) comprises an oligo/polysaccharide the monosaccharides of which are linked 1-2, 1-4, or 1-6.

8. A process as claimed in claim 1 wherein:
    oxidation of molecule (1) produces adjacent diols in aldehyde carbonyls with rupture of the interdiol carbon-carbon bond;
    a periodate of an alkaline or alkaline-earth metal is used as the oxidizing agent;
    the concentration of periodate is such that a minimum of 20% of the adjacent diols are oxidized;

the reaction occurs at a pH of between 7.0 and 9.0 and at a temperature of between 14° C. and 35° C.; and the oxidized polymer is purified of the oxidizing agent by a process selected from dialysis, ultrafiltration and gel filtration.

9. A process as claimed in claim 8 wherein the reaction must continue until between 20% and 90% of the adjacent diols have been oxidized.

10. A process as claimed in claim 1 wherein molecule (2) comprises an amino group which can react with the carbonyls to provide a Schiff base the absence of this reaction resulting in the elimination of the sulfonated group.

11. A process as claimed in claim 10 wherein the sulfonated group is one of the following group: aliphatic aminosulfate, taurine, cysteic acid.

12. A process as claimed in claim 1 wherein:
the reaction between oxidized molecule (1) and the molecule (2) occurs at a pH between 1.5 and 8.0;
the quantity of the oxidized molecule (1) used in the reaction is between 0.1 and 10 g $L^{-1}$;
the quantity of molecule (2) used in the reaction is selected such that the proportion of carbonyl groups of the molecule (1) to the amino groups of the molecule (2) is between 1:10 and 2:1;
the reaction temperature is between 85° C. and 110° C.; and
the reaction continues until the concentration of molecule (2) remains constant or is zero.

13. A process as claimed in claim 1 wherein the polymer carrying sulfonated groups present in the reaction mixture and obtained as a result of said reaction is purified of reagents by a process selected from gel filtration, ultrafiltration, dialysis and precipitation with solvents.

14. A process as claimed in claim 1 wherein polymers carrying sulfonated groups present antiviral activity and a low or non-existent level of anticoagulant activity and of toxicity, suitable for use as pharmaceuticals for human and veterinary use.

15. A polymer with antiviral activity produced by the process of claim 1.

* * * * *